United States Patent [19]

Strohmeyer et al.

[11] 3,932,523
[45] Jan. 13, 1976

[54] PROCESS FOR PREVENTING THE FORMATION OF AN EMULSION WHEN WORKING UP REACTION MIXTURES CONTAINING BUTYRALDEHYDES AND COBALT

[75] Inventors: Max Strohmeyer, Limburgerhof; Helmut Walz, Ludwigshafen; Max Appl, Dannstadt-Schaurnheim; Hans Moell, Heidelberg; Horst Kerber, Ludwigshafen; Heinz Hohenschutz, Mannheim, all of Germany

[73] Assignee: BASF Aktiengesellschaft, Ludwigshafen (Rhine), Germany

[22] Filed: Jan. 20, 1975

[21] Appl. No.: 542,709

[30] Foreign Application Priority Data
Feb. 1, 1974 Germany.............................. 2404855

[52] U.S. Cl. ..................... 260/604 HF; 260/632 HF
[51] Int. Cl.$^2$.......................................... C07C 45/08
[58] Field of Search............................... 260/604 HF

[56] References Cited
UNITED STATES PATENTS
3,520,937   7/1970   Moell et al. .................. 260/604 HF Primary Examiner—James O. Thomas, Jr.
Assistant Examiner—R. H. Liles
Attorney, Agent, or Firm—Johnston, Keil, Thompson & Shurtleff

[57] ABSTRACT

The formation of an emulsion when working up reaction mixtures containing butyraldehydes and cobalt is avoided by a treatment with gases containing molecular oxygen in an aqueous acid medium at an elevated temperature, at least twice the amount of molecular oxygen stoichiometrically required for the oxidation of the cobalt being used per gram atom of cobalt present in the oxoreaction mixture.

7 Claims, No Drawings

PROCESS FOR PREVENTING THE FORMATION OF AN EMULSION WHEN WORKING UP REACTION MIXTURES CONTAINING BUTYRALDEHYDES AND COBALT

This application discloses and claims subject matter described in German Patent Application P 24 04 855.3, filed Feb. 1, 1974, which is incorporated herein by reference.

The invention relates to a process for preventing the formation of an emulsion when working up reaction mixtures containing aldehydes and cobalt by treatment with gases containing molecular oxygen in an aqueous acid medium at an elevated temperature, followed by separation of the aqueous phase containing cobalt.

U.S. Pat. Nos. 2,547,178 and 3,520,937 disclose processes in which oxo reaction mixtures containing aldehydes and cobalt are worked up by treatment with air in the presence of aqueous acid at an elevated temperature, in order to remove the cobalt contained in the oxo reaction mixture. The aqueous acid phase containing cobalt is then separated from the cobalt-free oxoreaction product, for example by decanting. However, emulsification frequently occurs between the oxo reaction product and the aqueous phase so that phase separation requires considerable time. Addition of extraneous substances to speed up phase separation and break the emulsion is inadvisable since, firstly, undesirable impurities may be introduced into the oxo product whilst, secondly, water-soluble additives would interfere with the re-use of the aqueous phase, containing cobalt, as a catalyst solution for the oxo reaction.

It is an object of the present invention to prevent the formation of emulsions when working up reaction mixtures containing butyraldehydes and cobalt, and at the same time to avoid undesirable side-effects.

We have found that the formation of an emulsion when working up oxo reaction mixtures containing butyraldehydes and cobalt by treatment with gases containing molecular oxygen in an aqueous acid medium at an elevated temperature, followed by separation of the aqueous phase containing cobalt, can be avoided advantageously by using, per gram atom of cobalt contained in the oxo reaction mixture, at least twice the amount of molecular oxygen stoichiometrically required for the oxidation of the cobalt.

The new process has the advantage that the formation of an emulsion can be prevented simply, and without adding extraneous substances.

The new process is noteworthy because, in treating oxo reaction mixtures with gases containing molecular oxygen to remove cobalt, as little excess oxygen as possible, over the amount required for the oxidation of the cobalt, is used, in order to minimize the oxidation of the aldehydes. It was not to be expected that the use of at least twice the stoichiometric amount of molecular oxygen per gram atom of cobalt would prevent formation of an emulsion since the effect of the amount of molecular oxygen used on emulsion formation was unforeseeable.

The starting mixtures used are oxo reaction mixtures obtained, eg., by reaction of propylene with carbon monoxide and hydrogen in an oxo reaction at from 100° to 180°C, especially at from 120° to 170°C, under pressures of from 100 to 400 atmospheres, in particular from 150 to 300 atmospheres, in the presence of 0.01 to 2 per cent by weight of cobalt carbonyl and cobalt carbonyl-hydride as catalysts. Such reaction mixtures in general contain from 60 to 95 per cent by weight of butyraldehydes and from 5 to 40 per cent by weight of alcohols, each with one carbon atom more than the starting olefin, and 0.01 to 2 per cent by weight of cobalt in the form of cobalt carbonyl and cobalt carbonyl-hydride. In these figures, the content of dissolved unconverted olefins, of carbon monoxide and of hydrogen, has been left out of account. A typical reaction mixture resulting from the hydroformylation of propylene contains, eg., from 70 to 90 per cent by weight of butyraldehydes, from 10 to 20 per cent by weight of butanols, from 3 to 8 per cent by weight of high-boiling constituents and from 0.005 to 1.5 per cent by weight of cobalt.

The oxo reaction mixtures are treated with gases containing molecular oxygen. Preferably, gases which contain from 15 to 25 per cent by volume of molecular oxygen are used. In addition, the gases can contain inert constituents such as nitrogen, argon or carbon dioxide. The use of air is of particular importance in industrial operation.

It is an essential feature of the invention that at least twice, and preferably 2.1 times, the amount of molecular oxygen stoichiometrically required for the oxidation of cobalt carbonyl to divalent cobalt is used per gram atom of cobalt present in the oxo reaction mixture. If, eg., air is used as the oxidant at least 2.7 cubic meters (S.T.P.) of air are used per kg of cobalt present in the reaction mixture. Preferably, the amount of molecular oxygen used should not exceed 2.5 times the stoichiometrically required amount since a large excess of molecular oxygen causes excessive oxidation of the valuable aldehydes, to less valuable carboxylic acids.

The treatment is carried out in an aqueous acid medium. In general, the weight of water used is from 0.1 to 10 times that of the oxo reaction mixture, advantageously from 0.1 to an equal amount. The pH of the aqueous acid medium used is generally from 2 to 6, and in particular from 3 to 5. Since the oxo reaction mixture itself is slightly acid because of the lower carboxylic acids contained therein, the addition of acids is frequently superfluous. However, it is advantageous to add small amounts of a non-oxidizing inorganic or organic acid, but it is advantageous to use lower fatty acids, especially those of which the cobalt salt is directly suitable for use as the catalyst for the oxo reaction. The use of formic acid and acetic acid has proved particularly successful. The amount of acid should at least suffice to convert the entire cobalt to the corresponding cobalt salt. The amount of water should preferably be such that during the treatment, and during the subsequent recycling of the aqueous solution, resulting from the treatment, to the reaction zone, the cobalt salts remain in solution and do not crystallize out. Since at one and the same time this solution which can be used as the catalyst should not be too dilute, whilst a considerable amount of water is required for the treatment, it is desirable to recycle the aqueous solution, containing cobalt, to the treatment chamber and only to tap off a small proportion, which is re-used as the catalyst solution for the oxo reaction.

The treatment is carried out at elevated temperatures, generally of from 60° to 160°C. Temperatures of from 80° to 150°C have proved particularly suitable and the results are particularly good at temperatures of from 105° to 140°C.

The residence time in the treatment chamber can vary within wide limits, depending on the treatment temperature. However, in general the times required are not more than one minute. Depending on the degree of mixing and the temperature used the organic phase of the reaction mixture is practically free from cobalt after only a few seconds and frequently within fractions of a second.

The treatment can be carried out at atmospheric or superatmospheric pressure. The latter, eg. pressures of more than 1 atmosphere gauge, and in particular of from 5 to 50 atmospheres gauge, has proved particularly suitable.

It has proved particularly desirable to carry out the treatment immediately after the production of the oxo reaction mixture, since longer residence times and storage times before treatment have an adverse effect on the quality of the product. Preferably, therefore, the oxo reaction mixture leaving the reactor is released directly into the treatment chamber whilst simultaneously introducing gases containing molecular oxygen, and the aqueous acid medium. The gases, which are dissolved in the mixture whilst it is under pressure, cause the mixture to atomize as the pressure is reduced, so that thorough mixing results.

The next stage after the treatment is preferably to separate the gas phase and liquid phase from one another. The aqueous phase is then separated from the organic phase, for example by decanting, and the organic phase is worked up by conventional methods, eg. by distillation, if necessary after washing it with water. The aqueous phase can be recycled to the treatment chamber. When it has reached a sufficient cobalt content, for example from 0.8 to 1.0 per cent by weight, it can be used directly as the catalyst solution for the oxo reaction.

The Examples which follow illustrate the process according to the invention.

EXAMPLE 1

8,900 kg of an oxo reaction mixture which contains 84% by weight of n- and i-butyraldehyde, 11% by weight of n- and i-butanol and 0.09% by weight of cobalt as cobalt carbonyl and cobalt carbonylhydride, and which is withdrawn from the oxo synthesis stage at a temperature of 150°C and a pressure of 290 atmospheres gauge, are passed hourly into a treatment chamber of 39 l capacity, wherein the pressure acting on the mixture is lowered from 280 atmospheres gauge to 17 atmospheres gauge. At the same time, 9,000 l of water, which contains 1.8% by weight of formic acid and 0.9% by weight of cobalt as cobalt formate and is at pH 3.9, and 23 cubic meters (S.T.P.) of air are passed hourly into the treatment chamber. The temperature in the chamber assumes a value of 115°C; the residence time is 1.5 seconds. 34 l (S.T.P.) of molecular oxygen are used per g atom of cobalt. This is 2.1 times the amount stoichiometrically required for the oxidation of the cobalt. The gas phase is separated from the resulting mixture. The liquid phase which remains separates, in the course of 2 seconds, into an organic phase and an aqueous phase. The organic phase, which contains 1 ppm of cobalt (which represents the limit of analytical detection) is worked up by distillation, without having been washed with water, whilst the aqueous phase is recycled. A portion of the aqueous phase is withdrawn for use as catalyst solution and the corresponding portion is replaced.

EXAMPLE 2 (comparative example)

The procedure followed is as described in Example 1 but only 20 cubic meters (S.T.P.) of air are used. This corresponds to 1.85 times the amount stoichiometrically required for the oxidation of the cobalt. The liquid phase forms an emulsion which has not separated into its phases even after 6 hours.

What we claim is:

1. In a process for preventing the formation of an emulsion when working up an oxo reaction mixture containing a butyraldehyde and cobalt by treatment with a gas containing molecular oxygen in an aqueous acid medium at an elevated temperature of from 60° to 160°C, followed by separation of the aqueous phase containing cobalt, the improvement comprising using at least twice the amount of molecular oxygen stoichiometrically required for the oxidation of the cobalt per gram atom of cobalt present in the oxo reaction mixture.

2. A process as claimed in claim 1 wherein from 2.1 to 2.5 times the stoichiometric amount of molecular oxygen is used.

3. A process as claimed in claim 1 wherein the oxo reaction mixture is derived from the reaction of propylene with carbon monoxide and hydrogen in the presence of cobalt carbonyl and contains 60 to 95 per cent by weight of butyraldehydes, 5 to 40 per cent by weight of alcohols and 0.01 to 2 per cent by weight of cobalt in combined form.

4. A process as claimed in claim 1 wherein the gas containing molecular oxygen contains 15 to 25 per cent by volume thereof.

5. A process as claimed in claim 1 wherein the treatment is carried out at a pH of the aqueous acid medium of 3 to 5, using from 0.1 to 10 parts by weight of water per part by weight of oxo reaction mixture.

6. A process as claimed in claim 1 wherein the treatment is carried out at a temperature of from 105° to 140°C.

7. A process as claimed in claim 1 wherein the oxo reaction mixture is treated directly after leaving the oxo reactor.

* * * * *